United States Patent [19]

Harris

[11] Patent Number: 4,627,439

[45] Date of Patent: Dec. 9, 1986

[54] PREBENT VENTRICULAR/ATRIAL CARDIAC PACING LEAD

[75] Inventor: Donald L. Harris, Key Largo, Fla.

[73] Assignee: Cordis Corporation, Miami, Fla.

[21] Appl. No.: 672,334

[22] Filed: Nov. 16, 1984

Related U.S. Application Data

[63] Continuation-in-part of Ser. No. 561,648, Dec. 15, 1983.

[51] Int. Cl.[4] .............................................. A61N 1/00
[52] U.S. Cl. ................................ 128/419 P; 128/785
[58] Field of Search .................... 128/419 P, 784, 785, 128/786

[56] References Cited

U.S. PATENT DOCUMENTS

| | | | |
|---|---|---|---|
| 4,057,067 | 11/1977 | Lajos | 128/419 P |
| 4,154,247 | 5/1979 | O'Neill | 128/419 P |
| 4,289,144 | 9/1981 | Gilman | 128/419 P |
| 4,401,126 | 8/1983 | Reenstierna | 118/63 |
| 4,493,329 | 1/1985 | Crawford et al. | 128/419 P |

FOREIGN PATENT DOCUMENTS 0126981  5/1984  European Pat. Off. ........ 128/419 P

OTHER PUBLICATIONS

"The Porous-Surfaced Electrode", MacGregor et al., The Journal of Thoracic and Cardiovascular Surgery, St. Louis, vol. 78, No. 2, pp. 281-291, Aug., 1979.
"A Variation on the Introducer Technique for Unlimited Access to the Unlimited Access to the Subclavian Vein", Belott, PACE, vol. 4, pp. 43-48, Jan.-Feb., 1981.
"Routine Implantation of Permanent Transvenous Pacemaker Electrodes in Both Chambers, A Technique Whose Time has Come", Parsonnet, PACE, vol. 4, pp. 109-112, Jan.-Feb., 1981.
"Transvenous Physiological Pacing—A New Atrioventricular Electrode", PACE, vol. 5, pp. 264-267, Mar.-Apr., 1982, Lajos.

Primary Examiner—Kyle L. Howell
Assistant Examiner—Randy Citrin
Attorney, Agent, or Firm—Lockwood, Alex, Fitzgibbon & Cummings

[57] ABSTRACT

A lead for effecting either or both of ventricular or atrial cardiac pacing and an assembly method are provided. The lead has a portion that is molded with a prebent condition which enables the proper positioning of the atrial electrode and of the ventricular electrode within the heart, while also enhancing the maintenance of such leads at their respective implanted positions. The lead includes an unbranched length along which are mounted both at least one ventricular electrode and at least one atrial electrode, each electrode being secured to respective distal ends of coil conductors of a multifilar coil within an insulating sheath.

12 Claims, 14 Drawing Figures

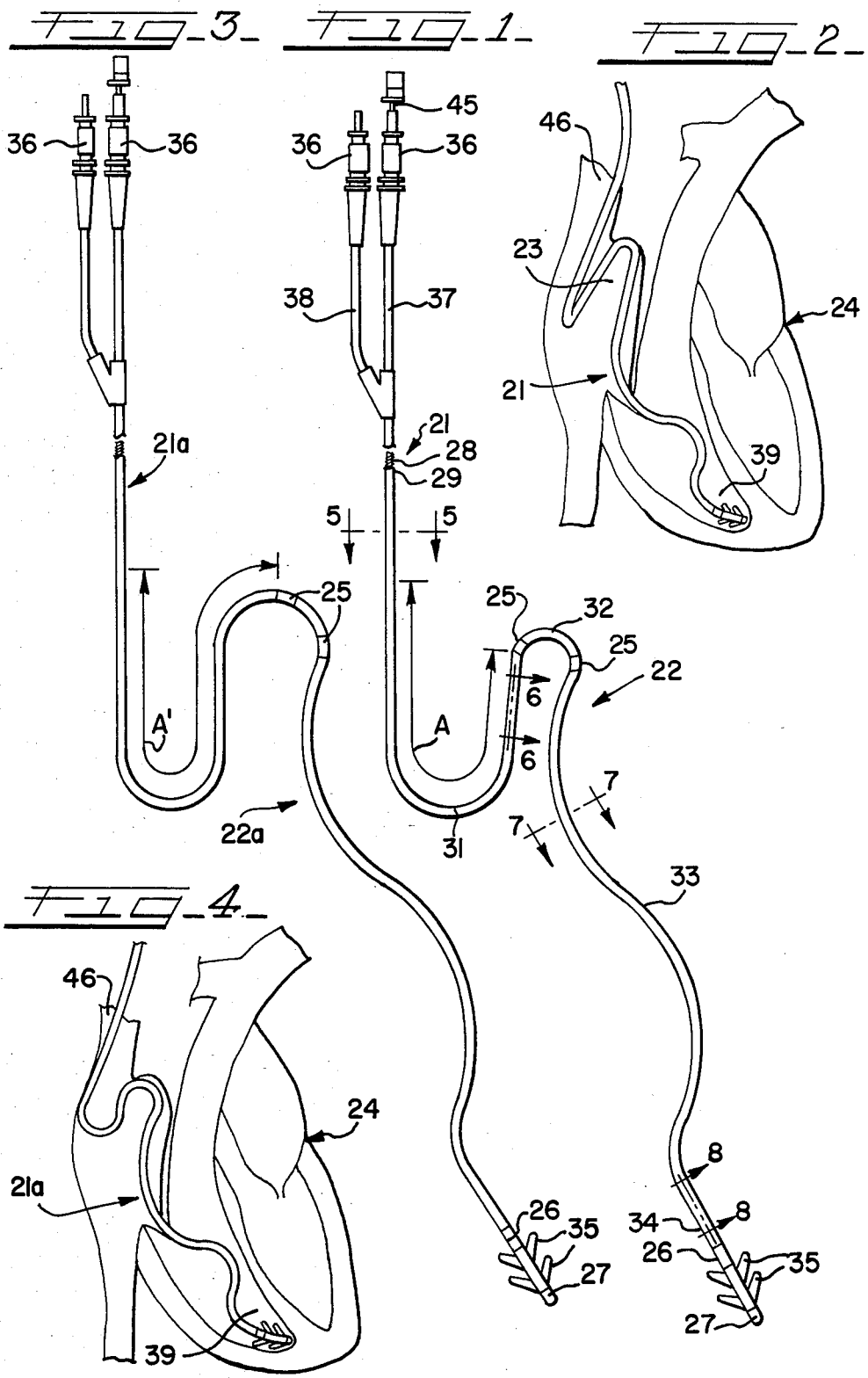

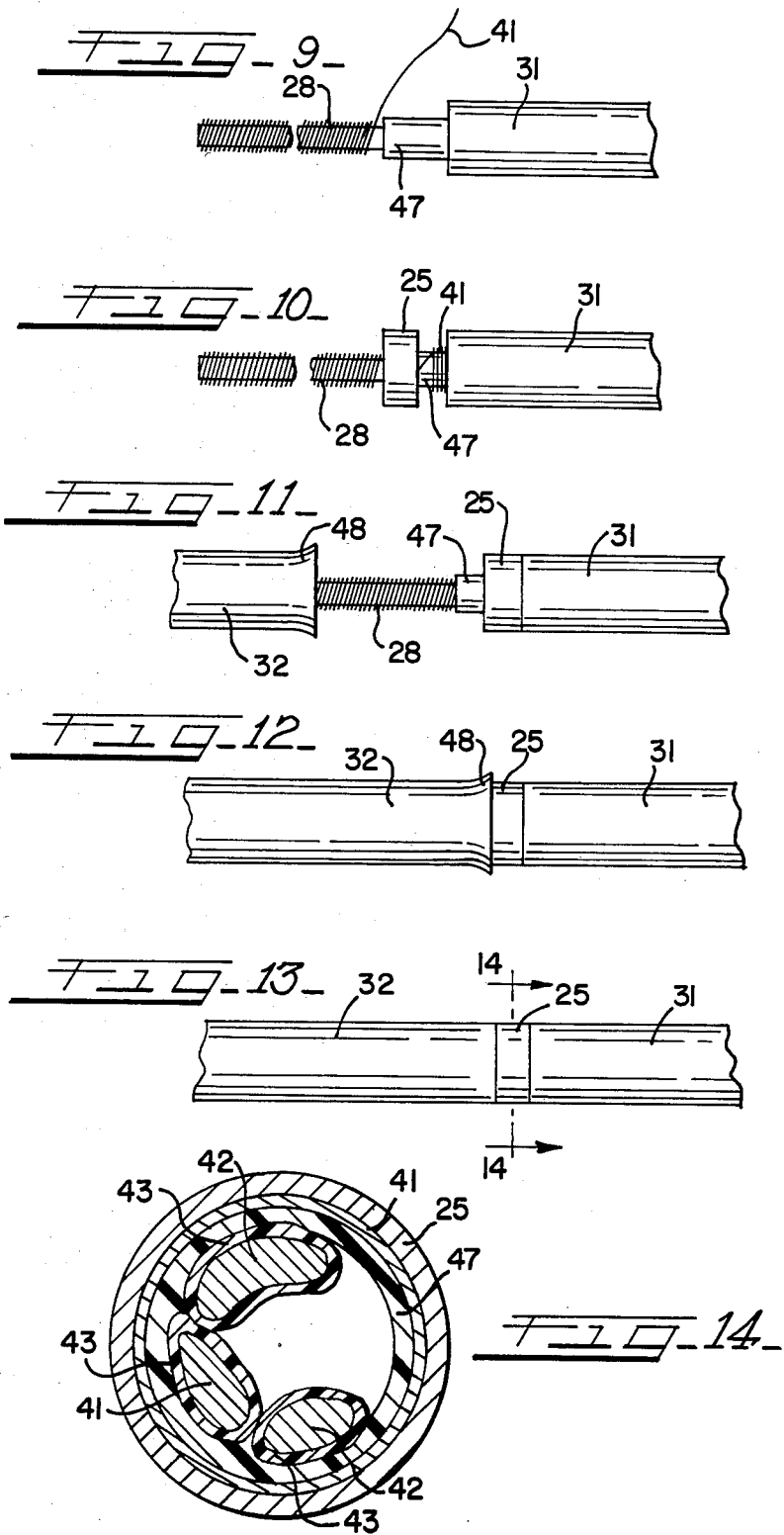

PREBENT VENTRICULAR/ATRIAL CARDIAC PACING LEAD

DESCRIPTION

This is a continuation-in-part of application Ser. No. 561,648, filed Dec. 15, 1983.

This invention generally relates to electrical leads for cardiac pacing or diagnosis, and more particularly to cardiac leads that stimulate and/or sense appropriate chambers of the heart, especially to devices that have both a ventricular lead and an atrial lead and to aspects relating to the assembly thereof. In an important aspect of the device according to this invention, such includes a preshaped, prebent elongated sheath having an unbranched length along which at least one ventricular electrode and at least one atrial electrode are positioned. The preshaped, prebent elongated flexible insulating sheath is structured such that the atrial lead and the ventricular lead are urged to maintain their respective implanted positions.

There has recently been an increased interest in pacemaker leads that provide for dual-chamber pacing by which it is possible to carry on pacing in either or both of an atrium and/or a ventricle of the heart. In these instances, such is often accomplished by providing two separate elongated conductors that are implanted in substantially side-by-side relationship within a single vein such as a subclavian vein. In some implantation procedures, access is gained through a cephalic vein or an external jugular vein. It is advantageous to avoid two separate incisions to provide access to the vein both for the conductors and for each introducer device therefor, and pacer leads have been developed by which two electrodes can be inserted through the same vein, for example including the use of introducing sheaths that are inserted through a single incision and into the same vein.

Even with such improved techniques and devices, it is often difficult for the surgeon to accurately position the ventricular lead and the atrial lead at their respective desired implantation locations. These efforts can be further complicated when the atrial lead and the ventricular lead are tied together or slide over one another, to the extent that movement of one lead in an effort to properly position same can detrimentally affect positioning of the other lead, requiring the surgeon to carry out a plurality of manipulative movements of the pacemaker lead in order to effect proper implantation. Also, leads that have portions of enlarged diameter have the disadvantage that the vein through which the lead is passed must be able to accommodate the largest diameter of the lead, thereby substantially offsetting the advantage gained by having an otherwise thin lead.

By the present invention, it is possible to readily locate and accurately implant both atrial electrodes and ventricular electrodes, due in large measure to a specifically prebent or preshaped condition of the lead onto which one or more atrial electrodes and one or more ventricular electrodes are mounted. This prebent or preshaped condition is such that, when the lead is implanted, the atrial and ventricular electrodes are urged, by the flexibility and positioning of the lead, in a manner to assist in stabilizing the maintenance of the electrodes at their respective desired implantation locations. The preshaped, prebent portion of the lead is molded such that it has a non-linear, multiply curved configuration, the curved portion of the lead immediately proximal of the most proximal atrial electrode preferably having enhanced memory for its preshaped characteristic by virtue of having its insulating sheath exhibit a greater degree of stiffness than does the insulating sheath for the remainder of the lead, while at the same time maintaining a substantially constant external diameter throughout the length of the lead. In addition, the preshaped, prebent portion of the lead has all of its electrodes positioned on an unbranched length thereof, rather than being bifurcated into an atrial branch and a ventricular branch. Such attributes are facilitated by providing the conductors within the sheath in the form of a multifilar coil having a plurality of coaxially wound coil conductors alternately interwound with each other, with each coil conductor for each atrial electrode terminating at the atrial electrode while each coil conductor for each ventricular electrode extends distally of the atrial electrode.

It is accordingly a general object of the present invention to provide an improved ventricular/atrial lead for cardiac pacing or diagnosis.

Another object of this invention is to provide an improved endocardial lead having a distal portion that is molded to have a prebent or preshaped condition so as to impart a plurality of implantation forces in order to enhance the securement of the lead in its implanted orientation.

Another object of this invention is to provide an improved cardiac lead for dual chamber pacing and diagnosis which utilizes a prebent or preshaped condition for providing forces along inner walls of the heart or adjoining tissues.

Another object of this invention is to provide an improved pacing lead that imparts minimum column forces onto the implanted electrodes and into the tissue within which each is implanted.

Another object of the present invention is to provide an improved pervenous or transvenous pacing lead having a distal portion that has a premolded shape which is generally curved and which is a single, unbranched length having oppositely curved sections that are consecutive interacting curves.

Another object of this invention is to provide an improved ventricular/atrial prebent lead for cardiac pacing and diagnosis, including means for assembling the device and the electrodes thereto.

Another object of the present invention is to provide an improved ventricular/atrial prebent lead for cardiac pacing and diagnosis which has an external diameter that is substantially constant throughout the length thereof while including a section exhibiting a greater degree of stiffness than other portions of the lead.

Another object of this invention is to provide an improved ventricular/atrial prebent lead for cardiac pacing or diagnosis in which its conductors are in the form of a multifilar coil.

Another object of this invention is to provide an improved small diameter ventricular/atrial pre-bent cardiac pacing lead with high tensil strength and good moisture resistance.

These and other objects of the present invention will become apparent from the following detailed description thereof, taken in conjunction with the accompanying drawings, wherein:

FIG. 1 is an elevational view of the preferred embodiment of the prebent or preshaped lead in accordance with this invention, shown in its molded, relaxed condition;

FIG. 2 is a drawing of a human heart illustrating the lead shown in FIG. 1 when fully implanted therewithin;

FIG. 3 is an elevational view of another embodiment of the prebent or preshaped lead in accordance with this invention, shown in its molded, relaxed condition;

FIG. 4 is a drawing of a human heart illustrating the lead of FIG. 3 in a fully implanted condition;

FIGS. 9, 10, 11, 12 and 13 are elevational views of sequential steps in the assembly of an electrode onto the lead in accordance with this invention; and FIG. 14 is a transverse cross-sectional view along the line 14—14 of FIG. 13.

Figure 5:
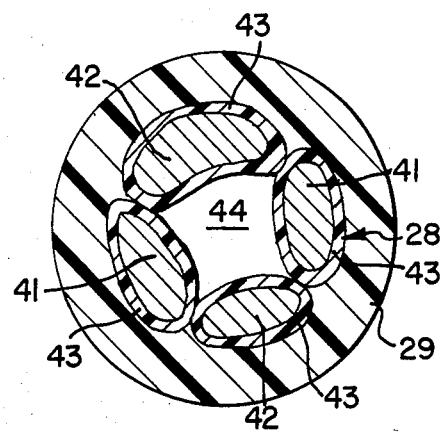
FIG. 5 is a transverse cross-section along the line 5—5 of FIG. 1.
Figure 6:
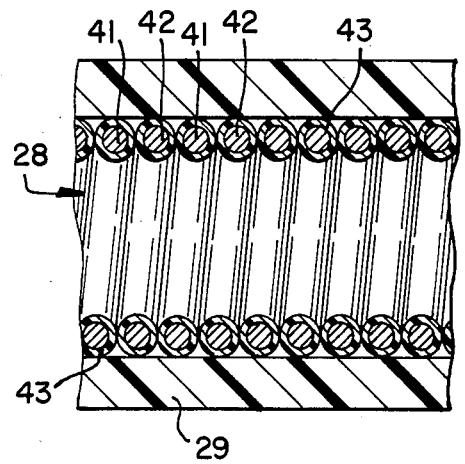
FIG. 6 is a longitudinal cross-section along the line 6—6 of FIG. 1.
Figure 7:
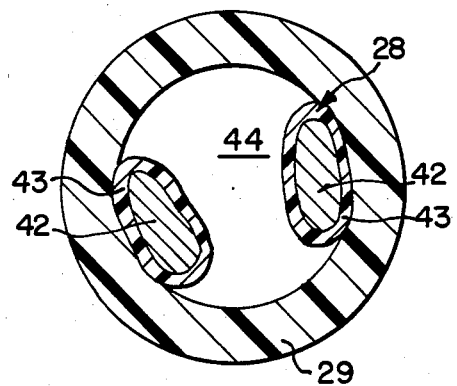
FIG. 7 is a transverse cross-section along the line 7—7 of FIG. 1.
Figure 8:
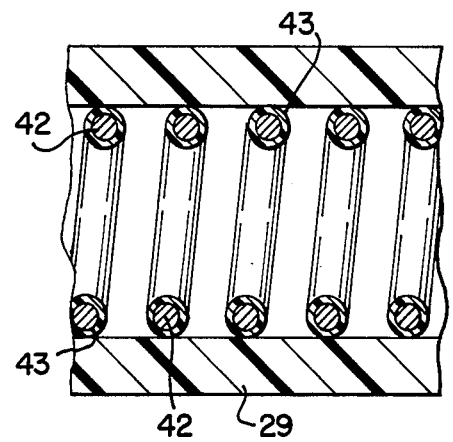
FIG. 8 is a longitudinal cross-section along the line 8—8 of FIG. 1.

The ventricular/atrial lead in accordance with this invention, generally designated as 21 in FIG. 1 and as 21a in FIG. 3, includes an unbranched, preshaped portion, generally designated as 22 in FIG. 1 and as 22a in FIG. 3. Ventricular/atrial leads 21 and 21a are substantially identical in structure, the principal difference being the extent of curvature thereof in the area of the atrial portion 23 of the heart, generally designated as 24 in FIGS. 2 and 4. Lead 21a is designed for hearts whose atrial appendage is missing. It is to be understood that, when reference is made herein to the ventricular/atrial lead 21, such also refers to the ventricular/atrial lead 21a, unless otherwise stated.

Unbranched preshaped, prebent portion 22 includes one or more atrial electrodes 25 and one or more ventricular electrodes 26, one of which is typically a tip electrode 27. Each such electrode 25, 26, 27, which is typically made of platinum, stainless steel, porous carbon or the like, is in electrical communication with one of the conductors of a multifilar coil 28, located within a preshaped, prebent elongated flexible insulating sheath 29. Multifilar coil 28 includes a plurality of coiled conductors that have low electrical resistance, and are very flexible and fatigue resistant, such as drawn braised strand silver coated Elgiloy wire having a diameter of about 0.003 inch to 0.005 inch.

The unbranched preshaped, prebent portion 22 is located at the generally distal end portion of the lead 21. Unbranched, prebent portion 22 is molded such that, when same is in its relaxed condition as illustrated in FIG. 1, this unbranched prebent portion 22 includes a number of consecutive curved sections that interact with each other, and are shaped as an integral unit having the consecutive curves, in order to achieve the advantageous properties that are characteristic of this invention, which include same being disposed toward self-seating during and after implantation within a human heart.

These interacting consecutive curved sections of the unbranched prebent portion 22 include an enhanced stiffness section 31 having a length and configuration designated as A in FIG. 1 and as A' in FIG. 3. This is joined to an atrial section 32 at which the atrial electrode(s) 25 are located. Enhanced stiffness section 31 and atrial section 32 combine to impart an overall tightly curved S-shape to this portion of the unbranched prebent portion 22, which is in the nature of a J-shaped atrial lead having its portion that contacts the atrial portion 23 of the heart 24 take the form of a generally arcuate length that curves generally oppositely of the J-shaped portion and away from the atrial portion 23.

Located distally of the atrial section 32 is an intermediate, generally S-shaped section 33 and a ventricular section 34 at which the ventricular electrode(s) 26, 27 are mounted, such combining to form an overall gradually curved S-shape. The overall tightly curved S-shape of the enhanced stiffness section 31 and the atrial section 32 combines with this overall gradually curved S-shape to form an unbranched prebent portion 22 that has the combined general configuration of two consecutive S-shaped curves.

Each of the atrial section 32, the intermediate S-shaped section 33 and the ventricular section 34 are typically made of the same material and each has substantially the same stiffness value, which stiffness value is more pliable and less stiff than the enhanced stiffness section 31. Preferably, all of the enhanced stiffness section 31, the atrial section 32, the intermediate S-shaped section 33, and the ventricular portion 34 each have substantially the same external diameter, the difference in stiffness between the enhanced stiffness section 31 and the rest of the lead 21 being brought about by the use of a sheath material at the enhanced stiffness section 31 that has a stiffness value greater than that of the rest of the sheath, which thus has a greater flexibility than the enhanced stiffness section 31.

In the embodiment illustrated in FIGS. 1 and 2, the enhanced stiffness section 31 is substantially U-shaped, the atrial section 32 is generally arcuate, and the ventricular section 34 is generally linear, though flexible so as to be bendable with the intermediate S-shaped section 33. The embodiment illustrated in FIGS. 3 and 4 is similar, except the enhanced stiffness section 31a thereof may, if desired, have an oppositely directed return curve continuation of its basic U-shape.

Anchor fins 35 may be provided at the distal end of the lead in order to assist in implantation of the ventricular electrodes 26, 27. A terminal assembly 36 of generally known construction is attached to the proximal end of each of an atrial lead extension 37 and a ventricular lead extension 38. Each conductor of the multifilar coil 28 which is secured to and which terminates at an atrial electrode 25 is included within the atrial lead extension 37 and is in electrical engagement with its terminal assembly 36. Each conductor of the multifilar coil 28 which is in electrical communication with each ventricular electrode 26, 27 is included within the ventricular lead extension 38 and is in electrical engagement with its terminal assembly 36. In accordance with conventional techniques, the terminal assemblies 36 are provided for electrically connecting the lead 21 to a suitable diagnostic device or pacemaker (not shown). With this arrangement, a pacemaker will provide electrical stimulation within the atrium 23 and/or the ventricle 39 of the heart 24 in accordance with generally known procedures and techniques.

In this regard, it is important to accurately position the atrial electrode(s) 25 and the ventricular electrode(s) 26, 27 and to maintain such implanted position once it is initially established. While these atrial and ventricular electrodes may be of a self-attachment type, for example having a porous surface whereby ingrowth from the atrium 23 and from the ventricle 39 serves to enhance holding of the electrodes, such ingrowth is somewhat gradual, and the electrodes are susceptible of movement until adequate ingrowth has been established. The unbranched preshaped, prebent portion 22 is useful in this regard.

Multifilar coil 28 has each of its individual coaxially wound coil conductors, including atrial coil conductor(s) 41 and ventricular coil conductor(s) 42, encapsulated with an insulating coating 43, for example a polyimide. Four coil conductors are illustrated, and it is to be understood that a lesser or greater number, typically as many as ten or more, coil conductors may be included. A lumen 44 is substantially coaxial with the multifilar coil 28, which lumen 44 is unbranched and follows the preshaped, prebent configuration of the unbranched preshaped, prebent portion 22, including its exterior flexible insulating sheath 29 and its multifilar coil 28.

Lumen 44 accommodates a stylet 45 which is inserted into the lead 21 at the terminal assembly 36 and which can be passed therethrough and into the ventricular section 34. Preferably, the stylet 45 has a distal end ball tip and has a reduced diameter immediately proximal of the ball tip in order to provide an especially flexible distal end that can readily follow the various reversing curves of the prebent portion 22.

In order to effect implantation of the ventricular/atrial lead 21 in a typical surgical procedure, the lead 21 is passed through a vein in order to gain access to the superior vena cava 46 for subsequent access to the right atrium 23 and to the right ventricle 39. Typically, the surgeon gains access to a suitable vein such as a subclavian, cephalic or external jugular vein by surgical incision at a suitable location. In many instances, access to the vein at the surgical incision is enhanced by an introducer sheath or the like (not shown) in accordance with known techniques. The lead 21 is then passed through the introducer sheath and through the vein which opens into the superior vena cava 46.

During this passage through the vein, it is necessary to stiffen the lead 21 while also substantially straightening the preshaped or prebent portion 22. Such is accomplished by the insertion of the stylet 45 into the lumen 44 and into the ventricular section 34. With the stylet 45 thus inserted therewithin, the lead 21, after having been inserted through the appropriate vein to the superior vena cava 46 is advanced into the atrium 23. Stylet 45 is then partially withdrawn until distal portions of the prebent configuration reform to the extent needed to manipulate the lead 21 such that the ventricular section 34 and a portion of the intermediate, S-shaped section 33 enter the ventricle 39. At this point, the stylet 45 is typically again advanced to the ventricular section 34 which assists in positioning the lead into the ventricle 39 toward its seated location. When the lead 21 is appropriately thus positioned in the ventricle 39, the stylet 45 is withdrawn from the ventricular section 34 and from at least a portion of the intermediate, S-shaped section 33, permitting sections 33, 34 to substantially return to their respective preshaped configurations.

Stylet 45 is then further withdrawn from the atrial section 32 and from the enhanced stiffness section 31, at which time sections 31 and 32 generally return to their respective prebent configurations. At this stage, the lead 21 is further manipulated until the atrial section 32 gains access to and initially seats within the atrial portion 23. Stylet 45 is then removed completely, and the surgeon imparts some tension on the lead 21 in order to exert pressure on the atrial electrode(s) 25. Seating of the atrial section 32 within the atrium 23 may involve pushing, twisting and pulling movement of the lead 21 and typically results in a seated position at which the lead 21 is in slightly tensioned engagement with a wall of the superior vena cava 46 or closely spaced tissues, exemplary seatings in this regard being illustrated in FIG. 2 and in FIG. 4. At this stage, the lead 21 typically is secured at its exit from the vein, and the terminal assemblies 36 are connected to the pacing device.

Maintenance of the previously described seating in the atrium 23 and in the ventricle 39 is facilitated because the implanted preshaped structure is such that each of the ventricular section 34, the atrial section 32, and the portion of the lead 21 that contacts the superior vena cava or closely spaced tissue components each impart a slight force onto an internal portion of the tissue. Each of said forces results in generally opposing forces in order to assist in stabilizing the maintenance of these locations against the tissue walls.

With particular reference to the generally S-shape of the sections 33, 34 the overall generally J-shape of sections 31, and their reverse-curve connection 32, such shapes are particularly advantageous for exerting an implantation maintenance force onto a wall of the ventricle 39 and of the atrium 23, which respective forces are adequate to maintain implantation but not of such a magnitude as to create excessive column-type perforation forces which would be imparted by the electrodes 25, 26, 27 if these curved shapes were instead relatively straight. Additionally, the elongated gradually curved shape of the sections 33 and 34 provide a structure that substantially self-adjusts to accommodate hearts of various sizes. The overall tightly curved S-shape of sections 31 and 32 provide especially effective seating within the atrium 23, even in those situations where the atrial appendage had been sacrificed, for example in a patient that had undergone treatment utilizing a heart pump.

The preshaped, prebent elongated flexible insulating sheath 29 of the lead 21 is molded of a body-compatible material that is relatively strong yet somewhat pliable and soft, while being heat and pressure formable and bendable so as to allow shaping of the assembled lead 21. Preferred materials include polyurethanes, in particular Pellethane D-55 and D-75 (Upjohn). In accordance with a preferred aspect of this invention, the enhanced stiffness section 31 is made of substantially the same material as the rest of the sheath 29, except the material (for example Pellethane D-75) of enhanced stiffness section 31 is somewhat stiffer than the rest of the sheath 29 (for example Pellethane D-55) when the lead 21 is at body temperature. A preferred arrangement in this regard is to mold the entire sheath 29 of a polyurethane, except that enhanced stiffness section 31 thereof is made of a particular polyurethane that is formulated to exhibit somewhat greater stiffness than the polyurethane out of which the remainder of the sheath 29 is made. The entire sheath 29 has the same diameter, which may be as small as French 5 (0.066 inch or 1.67 mm) or less.

Typically, the lead 21 is made by having the sections assembled into sheath 29 or portion 22 inserted within a mold including a shaped section similar to that of the unbranched preshaped, prebent portion 22 or 22a, except each curve thereof typically has a greater degree of curvature than that shown in FIGS. 1 and 3. Such enhanced curvature is provided in order to insure that the unbranched preshaped portion 22 or 22a exhibits a shape such as that illustrated in FIG. 1 or FIG. 3, respectively, after the stylet 45 is inserted through and withdrawn from the unbranched preshaped portion 22, 22a.

Generally speaking, because the tip ventricular electrode 27 engages the ventricle 39 in a substantially axial direction, it is important to avoid the development of excessive column-type forces, and the intermediate S-shaped section 33 and the ventricular section 34 are typically more flexible than the enhanced stiffness section 31 and the atrial section 32. This is achieved in part because of the gradually curving shape of sections 33 and 34 and also by virtue of the fact that each atrial coil conductor 41 terminates at an atrial electrode 25, with the result that there are fewer coil conductors in the multifilar coil 28 within the sections 33 and 34 than within the rest of the lead 21 (except for extensions 37 and 38), thereby reducing the resistance to bending of the sections 33 and 34 when compared with sections 31 and 32.

With more particular reference to the anchor fins 35, especially suitable are very thin polymeric fins positioned on generally opposite sides of the ventricular section 34. Exemplary fins are made of 0.001 to 0.002 inch thick polyurethane. Anchor fins 35 of this type securely stabilize the ventricular electrodes 26, 27 in position while allowing removal when desired in the future by twisting the lead 21 thereby winding the anchor fins 35 around the ventricular section 34. This twisting procedure generally pulls the anchor fins 35 from their imbedded location. This approach is also very useful for eliminating tricuspid valve entrapment and position changing problems, and it allows for entry of a finned lead through relatively small entrance vessels and introducing sheaths.

FIGS. 9 through 14 generally illustrate the preferred approach that is taken in order to join the various sections of the lead 21, these drawings particularly illustrating the situation when such joining includes the incorporation of a ring electrode 25, 26 thereat, and it is to be understood that substantially the same assembly arrangement is suitable for joining the various sections together at a location that does not include a ring electrode. The assembly illustrated in the drawings is that of the atrial electrode 25, the enhanced stiffness section 31, and the atrial section 32.

Referring to FIG. 9, a length of tubing adequate to form the atrial section 31 is positioned over the multifilar coil 28 with a close fitting mandrel in place, and an annular step 47 having an axial length greater than the axial length of the electrode 25 is formed at the end of the atrial section 31. Annular step 47 is preferably formed by using a heated die that imparts pressure and an elevated temperature to the end of the atrial section 31 that is adequate to reform the material into the coil thereof so that the annular step 47 is radially recessed and has an outer diameter that is less than that of the atrial section 31. After the formation of the annular step 47, the distal end of an atrial coil conductor 41 is uncoiled and stripped so as to remove its insulating coating 43. This permits the thus uninsulated section of the conductor 41 to be wrapped around the annular step 47. Preferably, the annular step 47 and wrapped conductor 41 are then coated with a conductive epoxy material, primarily to enhance the electrical contact between the conductor 41 and the electrode 25 but also to provide a moisture seal. The ring electrode 25 is then assembled over the annular step 47, wrapped conductor 41, and epoxy conductive material until same abuts with the unstepped portion of the atrial section 31, such movement being illustrated between FIG. 10 and FIG. 11.

Next, as illustrated between FIG. 11 and FIG. 12, the less stiff section 32, preferably having a cold-flared end 48, is assembled over the multifilar coil 28 until the flared end 48 engages and butts against the free edge of the electrode 25, such also covering the portion of the annular step 47 and conductor 41 that extends beyond the electrode 25. The cold-flared end 48 of this assembly is then reformed and fused to extension 47, typically by the application of heat and pressure by a suitable die arrangement, to the fully assembled configuration illustrated in FIGS. 13 and 14, such that the electrode 25 is generally flush with both the atrial section 32 and the enhanced stiffness section 31.

It will be apparent to those skilled in the art that various modifications are possible without departing from the spirit and scope of this invention; accordingly, this invention is to be construed only by the appended claims.

I claim:

1. A ventricular/atrial prebent lead for cardiac pacing or diagnosis, comprising:

a preshaped, prebent elongated flexible polymeric material insulating sheath having a distal end portion and a proximal end portion structured for connecting engagement with pacing equipment;

a multifilar coil encased within said preshaped, prebent elongated flexible sheath, said multifilar coil having a plurality of coaxially wound coil conductors alternately interwound with each other, each said coil conductor being insulated, each said coil conductor having a proximal end for electrically conductive engagement with the pacing equipment, and each said coil conductor having a distal end along an unbranched length of the preshaped, prebent elongated sheath, at least one of said distal ends defining an atrial coil conductor having a length shorter than at least one other coil conductor having its distal end defining a ventricular coil conductor;

an electrically conductive ventricular electrode at the distal end portion of said single unbranched length of the preshaped, prebent elongated sheath, said ventricular electrode being in electrically conductive communication with the distal end of said ventricular coil conductor;

an electrically conductive atrial electrode at an atrial location along said single, unbranched length of the preshaped, prebent elongated sheath, said atrial location being between the proximal end portion and the distal end portion of the sheath and being positioned for engaging an atrial portion of a heart within which the lead is implanted, and said atrial electrode is in electrically conductive communication with said shorter length atrial coil conductor; and wherein said unbranched length of the prebent elongated flexible polymeric material sheath includes a flexible enhanced stiffness section that is made of a polymeric material which is stiffer than the polymeric material out of which the remainder of the unbranched length is made, said flexible enhanced stiffness section having an outer diameter substantially the same as that of the remainder of the unbranched length.

2. The ventricular/atrial prebent lead according to claim 1, wherein said unbranched length of the preshaped, prebent elongated sheath includes a plurality of consecutive curved sections.

3. The ventricular/atrial prebent lead according to claim 1, wherein said unbranched length of the preshaped, prebent elongated sheath includes a plurality of consecutive curved sections that have a combined general configuration of two consecutive S-shaped curves.

4. The ventricular/atrial prebent lead according to claim 1, wherein said unbranched length of the preshaped, prebent elongated sheath includes a plurality of consecutive curved sections, including said enhanced stiffness section and an atrial section adjacent thereto that combine to form an overall tightly curved S-shape.

5. The ventricular/atrial prebent lead according to claim 1, wherein said unbranched length of the preshaped, prebent elongated sheath includes a plurality of consecutive curved sections, including said enhanced stiffness section and an atrial section adjacent thereto that combine to form an overall tightly curved S-shape including a J-shaped atrial portion and a generally arcuate length that curves generally oppositely of the J-shaped atrial portion and generally toward a ventricular portion of the heart.

6. The ventricular/atrial prebent lead according to claim 1, wherein said unbranched length of the preshaped, prebent elongated sheath includes a plurality of consecutive curved sections, including an intermediate, generally S-shaped section and a ventricular section that combine to form an overall gradually curved S-shape.

7. The ventricular/atrial prebent lead according to claim 1, wherein said unbranched length of the elongated flexible sheath includes a generally curved atrial section distally adjacent to said enhanced stiffness section, and wherein said enhanced stiffness section is basically U-shaped.

8. The ventricular/atrial prebent lead according to claim 1, wherein said multifilar coil defines a lumen substantially coaxial therewith.

9. The ventricular/atrial prebent lead according to claim 1, wherein the prebent elongated flexible sheath has a substantially constant diameter.

10. The ventricular/atrial prebent lead according to claim 1, further including an anchor fin projecting from said sheath at a location generally adjacent to an electrode, said anchor fin being a thin polymeric member that is flexible generally onto the circumferential outer surface of said sheath.

11. The ventricular/atrial prebent lead according to claim 1, wherein said unbranched length of the preshaped, prebent polymeric material elongated sheath includes a plurality of consecutive sections,
an annular, radially recessed step is at an end of one of said consecutive sections; and
an inner surface of a leading end of another of said consecutive sections circumferentially engages and substantially fully covers said annular, radially recessed step.

12. The ventricular/atrial prebent lead according to claim 11, wherein
a free uninsulated conductor length of one of said coil conductors is wrapped
generally around said annular, radially recessed step;
an electode member is positioned over said annular, radially recessed step and said wrapped uninsulated conductor length and said electrode substantially covers at least the innermost length of said recessed step; and
said leading end of the another section is butted against said electrode member.

* * * * *